(12) United States Patent
Gudipati et al.

(10) Patent No.: US 7,161,004 B2
(45) Date of Patent: Jan. 9, 2007

(54) PROCESSES TO PRODUCE INTERMEDIATES FOR ROSUVASTATIN

(75) Inventors: Srinivasulu Gudipati, Hyderabad (IN); Srinivas Katkam, Secunderabad (IN); Rajeshwar Reddy Sagyam, Hyderabad (IN); Jaya Satyanaraya Kudavalli, West Godavari (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 9 days.

(21) Appl. No.: 11/157,552

(22) Filed: Jun. 21, 2005

(65) Prior Publication Data

US 2006/0004200 A1    Jan. 5, 2006

Related U.S. Application Data

(60) Provisional application No. 60/581,480, filed on Jun. 21, 2004.

(51) Int. Cl.
*C07D 239/42* (2006.01)
*C07D 319/06* (2006.01)

(52) U.S. Cl. ..................................... 544/297; 549/375
(58) Field of Classification Search ............... 544/297; 549/375

See application file for complete search history.

(56) References Cited

U.S. PATENT DOCUMENTS 5,260,440 A * 11/1993 Hirai et al. ................. 544/332

FOREIGN PATENT DOCUMENTS

WO          097614 A2  * 11/2003

* cited by examiner

*Primary Examiner*—Taofiq Solola
(74) *Attorney, Agent, or Firm*—Robert A. Franks; Edward D. Pergament; Milagros A. Cepeda

(57) ABSTRACT

Intermediate compounds for preparing rosuvastatin are prepared by a process comprising oxidizing hydroxy groups to aldehyde groups, using sodium hypochlorite and 2,2,6,6-tetramethyl piperidinyl oxy free radical (TEMPO) as a catalyst.

10 Claims, No Drawings

PROCESSES TO PRODUCE INTERMEDIATES FOR ROSUVASTATIN

INTRODUCTION TO THE INVENTION

The present invention relates to improved processes for the preparation of compounds having Formulas I and II,

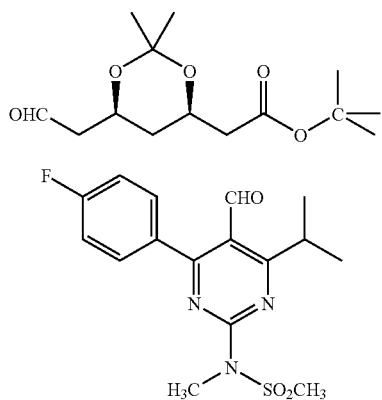

Formula I

Formula II which are useful for the preparation of rosuvastatin and its pharmaceutically acceptable salts.

Rosuvastatin, described chemically as [(E)-7-[4-(4-fluorophenyl)-6-isopropyl-2-[methyl(methylsulfonyl)amino]pyrimidin-5-yl](3R,5S)-3,5-dihydroxyhept-6-enoic acid] is a synthetic lipid-lowering agent. It is used commercially in the form of its calcium salt for the pharmaceutical products sold as CRESTOR™.

U.S. Pat. No. 5,260,440 describes rosuvastatin and its pharmaceutically acceptable salts. The process for the preparation of the rosuvastatin comprises condensing the intermediate compound of Formula II with methyl (3R)-3 (ter-butyidimethylsilyloxy)-5-oxo-6-triphenyl phosphoranylidene hexanate followed by desilylation of the resultant compound and further reduction of the obtained compound with sodium borohydride gives rosuvastatin, which is further converted into its salt.

According to U.S. Pat. No. 5,260,440, the intermediate compound of Formula II can be prepared by oxidation of the corresponding hydroxy compound by using an oxidizing agent like tetrapropylammonium perruthenate.

The process for the preparation of the compound of Formula II uses expensive chemicals like tetrapropylammonium perruthenate, which are not suitable for large-scale industrial applications.

Further, patent application No. WO 03/097614A2 describes a process for preparation of rosuvastatin and its pharmaceutically acceptable salts thereof. The process uses the hazardous and expensive chemicals like γ-manganese dioxide for the conversion of a hydroxy compound (a precursor of Formula II) to its corresponding aldehyde of Formula II. The process is not industrially feasible and also is economically expensive.

U.S. Pat. No. 4,970,313 describes a process for preparation of key intermediates of rosuvastatin and its related compounds. A process for the preparation of the Intermediate of Formula I involves oxidation of its corresponding hydroxy compound by using oxalylchloride. The process involves the hazardous and expensive chemicals like oxalylchloride, which is not feasible for scale up. This process is conducted at cryogenic temperatures like −78° C. which is industrially, economically not feasible and unsafe to handle.

These foregoing problems are avoided by the present invention, which is a convenient and cost-effective process for the preparation of compounds of Formulas I and II. The compounds of Formulas I and II are known for being particularly useful as intermediates for preparing pharmaceutically active substances, which are used as HMG CoA reductase inhibitors and antihypercholesterolemic agents, one among them is rosuvastatin.

SUMMARY OF THE INVENTION

A process for the preparation of tertiary butyl-2[(4R, 6S)-6-formyl-2,2-dimethyl-1,3-dioxan-4-yl] acetate comprising oxidation of corresponding hydroxy compound (4R-cis)-6-(hydroxymethyl)-2,2-dimethyl-1,3-dioxane-4-acetic acid, 1,1-dimethlethyl ester of Formula I using 2,2,6,6-tetramethyl piperidinyl oxy free radical (TEMPO) in the presence of sodium hypochlorite.

A process for the preparation of 4-(4-fluorophenyl)-6-isopropyl-2-(N-methyl-N-methylsulfonylamino)-5-pyrimidine carbaldehyde comprising oxidation of corresponding hydroxy compound [4-(4-flourophenyl)-6-isopropyl-2-(N-methyl-N-methylsulphonylamino)pyridin-5-yl] methanol of Formula II using 2,2,6,6-tetramethyl piperidinyl oxy free radical (TEMPO) in the presence of sodium hypochlorite.

DETAILED DESCRIPTION OF THE INVENTION

The present invention is directed towards a simple and commercially feasible process for preparation of compounds of Formulas I and II.

The present invention provides an improved, most cost effective, ecofriendly process for the preparation of compounds of Formulas I and II.

An embodiment of the present invention provides a process for the preparation of tertiary butyl-2[(4R,6S)-6-formyl-2,2-dimethyl-1,3-dioxan-4-yl]acetate (an intermediate of Rosuvastatin) of Formula I comprising oxidation of corresponding hydroxy compound (4R-cis)-6-(hydroxymethyl)-2,2-dimethyl-1,3-dioxane-4-acetic acid, 1,1-dimethlethyl ester of Formula III using 2,2,6,6-tetramethyl piperidinyl oxy free radical (TEMPO) and sodium hypochlorite in a suitable solvent, at temperatures less than about 20° C. A process of the present invention is schematically represented as follows:

SCHEME 1

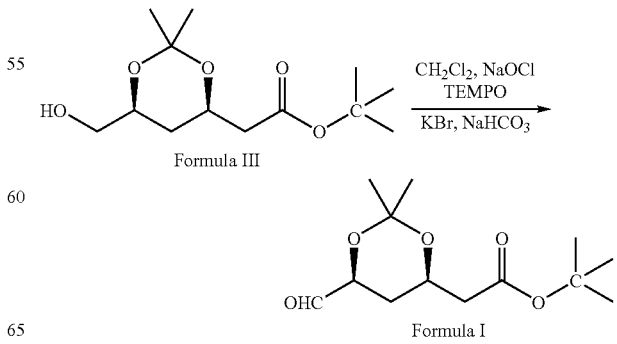

Accordingly, an embodiment of the process for the preparation of formula I comprises:
  i. Oxidation of (4R-cis)-6-(hydroxymethyl)-2,2-dimethyl-1,3-dioxane4-acetic acid, 1,1-dimethylethyl ester of Formula III using 2,2,6,6-tetramethyl piperidnyl oxy free radical (TEMPO) as a catalyst in the presence of potassium bromide, sodium bicarbonate, sodium hypochlorite in a suitable solvent such as, without limitation thereto, methylene chloride, tetrahydrofuran, toluene, dimethy-1sulfoxide, N,N-dimethylformaide, N,N-dimethylacetamide, preferably methylene chloride, at 0–5° C. until the reaction is complete, such as for 1–2 hours;
  ii. filtration of the reaction mass of step (i);
  iii. organic layer is separated from the filtrate of step (ii);
  iv. thus obtained organic layer of step (iii) is washed with 10% sodium thiosulfate solution;
  v. the organic layer of step (iv) saturated with sodium chloride solution;
  vi. finally the organic layer of step (v) evaporated to dryness at below 40° C. under reduced pressure to afford the desired compound tertiary butyl-2[(4R,6S)-6-formyl-2,2-dimethyl-1,3-dioxan-4-yl]acetate of Formula I.

The thus obtained compound of Formula I can be further used as an intermediate in the preparation of rosuvastatin.

Another embodiment of present invention relates to a process for the preparation of 4-(4-fluorophenyl)-6-isopropyl-2-(N-methyl-N-methylsulfonylamino)-5-pyrimidine carbaldehyde (an intermediate of rosuvastatin) of Formula II comprising oxidation of corresponding hydroxy compound [4-(4-flourophenyl)-6-isopropyl-2-(N-methyl-N-methylsulphonylamino)pyridin-5-yl] methanol of Formula IV using the catalyst 2,2,6,6-tetramethyl piperidnyl oxy free radical (TEMPO) and sodium hypochlorite in a suitable solvent, at temperatures less than about 20° C. A process of the present invention is schematically represented in Scheme 2, as follows:

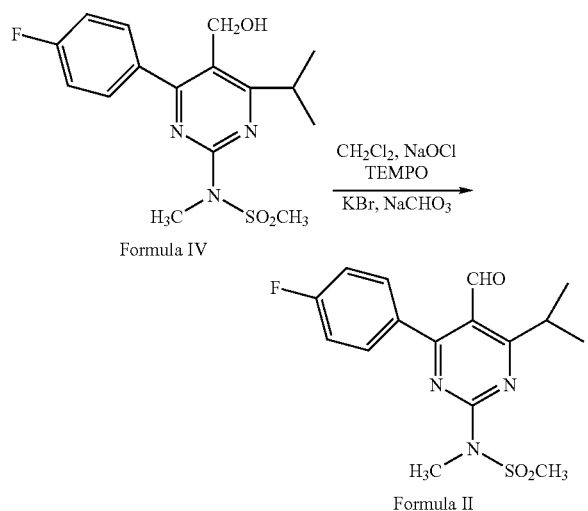

SCHEME 2

Formula IV

Formula II

The present invention also provides a simple and commercially feasible process for the preparation of compound of Formula II. The process in one embodiment comprises,
  i. oxidation of [4-(4-flourophenyl)-6-isopropyl-2-(N-Methyl-N-methylsulfonylamino)pyridin-5-yl] methanol of Formula IV using 2,2,6,6-tetramethyl piperidnyl oxy free radical (TEMPO) in the presence of potassium bromide, sodium bicarbonate, and sodium hypochlorite in a suitable solvent such as, without limitation thereto, methylene chloride, tetrahydrofuran, toluene, dimethylsulfoxide, N,N-dimethylformaide, N,N-dimethylacetamide, preferably methylene chloride at 0–5° C. until the reaction is complete, such as for 1–2 hours;
  ii. filtration of the reaction mass of step (i);
  iii. organic layer is separated from the filtrate of step (ii);
  iv. thus obtained organic layer of step (iii) is washed with 10% sodium thiosulfate solution;
  v. the organic layer of step (iv) is saturated with sodium chloride solution;
  vi. finally the organic layer of step (v) is evaporated to dryness at below 40° C. under reduced pressure to afford the desired compound 4-(4-flourophenyl)-6-isopropyl-2-(N-methyl-N-methylsulphonylamino)-5-pyrimidine carbaldehyde of Formula II.

The obtained compound of Formula II can be used for the preparation of rosuvastatin.

The process of the present invention is simple, well suited for industrial scale up, free from fire hazardous catalytic transformation, commercially viable, and a cost effective process.

The following examples are provided for the purpose of giving those skilled in the art a sufficiently clear and complete explanation of the present invention, but must not be deemed to be limitations on the essential aspects of the invention.

EXAMPLE 1

Preparation of Tert.butyl-2 [(4R,6S)-6-Formyl-2,2-dimethyl-1,3-dioxan-4-yl]acetate (Formula I)

2,2,6,6-tetramethyl piperidinyl oxy free radical (TEMPO) (0.2 g), potassium bromide (9.6 g) and sodium bicarbonate (90 g) were dissolved in methylene chloride (600 ml) and stirred the contents together at 0–5° C. A solution of (4R-cis)-6-(hydroxymethyl)-2,2-dimethyl-1,3-dioxane-4-acetic acid, 1,1-dimethylethyl ester of Formula III (100 g) in methylene chloride (400 ml) was added to the above solution at 0–5° C. To this solution 10% sodium hypochlorite solution (159 ml) (NaOCl) was added at 0–5° C. Again sodium bicarbonate (96 g) and followed by 10% sodium hypochlorite solution was added to the reaction mass. Reaction mass was maintained for 1–2 hours at 0–5° C. and filtered through perlite. The organic layer was separated and washed with 10% sodium thiosulfate solution (250 ml), then water (250 ml) followed by saturated sodium chloride solution (250 ml). Organic layer was distilled at below 40° C. under reduced pressure to afford the title product. Yield: 95 g.

EXAMPLE 2

Preparation of 4-(4-fluorophenyl)-6-isopropyl-2-(N-methyl-N-methylsulphonyl amino)-5-pyrimidinecarbaldehyde (Formula II)

2,2,6,6-tetramethyl piperidinyl oxy free radical (TEMPO) (5 mg), potassium bromide (0.385 g) and sodium bicarbonate (3.63 g) were dissolved in methylene chloride (150 ml) and stirred together at 0–5° C. A solution of 4-(4-flourophenyl)-6-isopropyl-2-(N-methyl-N-methylsulfonylamino)pyrimidin-5-yl]methanol (11 g) in methylene chloride (25 ml)

was added to the above solution at 0–5° C. To this solution 10% sodium hypochlorite solution (24.2 g) was added at 0–5° C. Reaction mass was maintained for 1–2 hours at 0–5° C. and filtered through perlite. Organic layer was separated and washed with 10% sodium thiosulfate solution (200 ml), water (200 ml) followed by saturated sodium chloride solution (150 ml). Organic layer was distilled off under reduced pressure and the title compound was isolated from the residue with cyclohexane (75 ml). Yield: 9.5 g.

The invention claimed is:

1. A process for preparing tertiary butyl-2[(4R, 6S)-6-formyl-2,2-dimethyl-1,3-dioxan-4-yl]acetate comprising oxidation of hydroxy compound (4R-cis)-6-(hydroxymethyl)-2,2-dimethyl-1,3-dioxane-4-acetic acid, 1,1-dimethlethyl ester using 2,2,6,6-tetramethyl piperidinyl oxy free radical (TEMPO) as a catalyst.

2. The process of claim 1 wherein an oxidizing agent comprises sodium hypochlorite.

3. The process of claim 1 wherein oxidation occurs in a solvent comprising methylenechloride, tetrahydrofuran, toluene, dimethylsulfoxide, N,N-dimethylformaide, or N,N-dimethylacetamide.

4. The process of claim 1 wherein the oxidation is conducted at temperatures less than about 20° C.

5. The process of claim 1 wherein oxidation is conducted at temperatures about 0–5° C.

6. A process for preparing 4-(4-fluorophenyl)-6-isopropyl-2-(N-methyl-N-methylsulfonylamino)-5-pyrimidine carbaldehyde comprising oxidation of hydroxy compound [4-(4-flourophenyl)-6-isopropyl-2-(N-methyl-N-methylsulphonylamino) pyridin-5-yl]methanol using 2,2,6,6-tetramethyl piperidinyl oxy free radical (TEMPO) as a catalyst.

7. The process of claim 6 wherein an oxidizing agent comprises sodium hypochlorite.

8. The process of claim 6 wherein oxidation occurs in a solvent comprising methylenechloride, tetrahydrofuran, toluene, dimethylsulfoxide, N,N-dimethylformaide, or N,N-dimethylacetamide.

9. The process of claim 6 wherein the oxidation is conducted at temperatures less than about 20° C.

10. The process of claim 6 wherein the oxidation is conducted at temperatures about 0–5° C.

* * * * *